(12) United States Patent
Fein et al.

(10) Patent No.: US 10,307,100 B2
(45) Date of Patent: Jun. 4, 2019

(54) METHODS AND SYSTEMS OF CONTROLLING A SUBJECT'S BODY FEATURE HAVING A PERIODIC WAVE FUNCTION

(71) Applicant: iFeel Healthy Ltd., Yavne (IL)

(72) Inventors: Elad Fein, Nofit (IL); Ryan Deluz, Beit Zaid (IL)

(73) Assignee: iFeel Healthy Ltd., Yavne (IL)

( * ) Notice: Subject to any disclaimer, the term of this patent is extended or adjusted under 35 U.S.C. 154(b) by 182 days.

(21) Appl. No.: 15/213,787

(22) Filed: Jul. 19, 2016

(65) Prior Publication Data

US 2017/0020443 A1 Jan. 26, 2017

Related U.S. Application Data

(63) which is a continuation of application No. 62/194,295, filed on Jul. 20, 2015.

(Continued)

(51) Int. Cl.
*A61B 5/024* (2006.01)
*A61B 5/00* (2006.01)
(Continued)

(52) U.S. Cl.
CPC ............ *A61B 5/486* (2013.01); *A61B 5/0022* (2013.01); *A61B 5/02405* (2013.01); *A61B 5/0402* (2013.01); *A61B 5/0476* (2013.01); *A61B 5/0488* (2013.01); *A61B 5/0816* (2013.01); *A61B 5/14517* (2013.01); *A61B 5/14532* (2013.01); *A61B 5/14539* (2013.01); *A61B 5/4833* (2013.01); *A61B 5/4836* (2013.01); *A61B 5/681* (2013.01); *A61M 21/00* (2013.01); *G06F 19/30* (2013.01); *G16H 20/30* (2018.01); *A61B 5/021* (2013.01); *A61B 5/02055* (2013.01); *A61B 5/02411* (2013.01); *A61B 5/02416* (2013.01); *A61B 5/0533* (2013.01); *A61B 5/7275* (2013.01); *A61B 2503/20* (2013.01); *A61M 2021/005* (2013.01); *A61M 2021/0027* (2013.01); *A61M 2021/0044* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2205/505* (2013.01); *A61M 2205/581* (2013.01); *A61M 2205/583* (2013.01); *A61M 2209/088* (2013.01); *A61M 2230/04* (2013.01); *A61M 2230/06* (2013.01); *A61M 2230/10* (2013.01); *A61M 2230/201* (2013.01);

(Continued)

(58) Field of Classification Search
CPC ... A61B 5/486; A61B 5/02405; A61B 5/0402; A61B 5/4833; A61B 5/7275; G16H 20/30; G16H 20/70; A61M 21/005; A61M 2205/502; A61M 2205/505; A61M 2205/581; A61M 2205/582; A61M 2205/583
See application file for complete search history.

(56) References Cited

U.S. PATENT DOCUMENTS

2015/0112606 A1* 4/2015 He .................... G06F 21/00
702/19

* cited by examiner

*Primary Examiner* — Paula J Stice
(74) *Attorney, Agent, or Firm* — Vorys, Sater, Seymour and Pease LLP (57) ABSTRACT

Provided is a method of controlling and adjusting at least one body feature of a subject using electronic mobile devices worked by a person in need thereof and measuring devices interconnected thereto.

3 Claims, 5 Drawing Sheets

Related U.S. Application Data

(60) Provisional application No. 62/315,750, filed on Mar. 31, 2016.

(51) Int. Cl.
| | |
|---|---|
| *A61B 5/0402* | (2006.01) |
| *A61B 5/0476* | (2006.01) |
| *A61B 5/0488* | (2006.01) |
| *A61B 5/145* | (2006.01) |
| *A61B 5/08* | (2006.01) |
| *A61M 21/00* | (2006.01) |
| *G06F 19/00* | (2018.01) |
| *G16H 20/30* | (2018.01) |
| *A61B 5/0205* | (2006.01) |
| *A61B 5/021* | (2006.01) |
| *A61B 5/053* | (2006.01) |
| *A63B 71/06* | (2006.01) |
| *A63B 24/00* | (2006.01) |
| *G16H 50/20* | (2018.01) |
| *G16H 20/70* | (2018.01) |

(52) U.S. Cl.
CPC .. *A61M 2230/205* (2013.01); *A61M 2230/208* (2013.01); *A61M 2230/30* (2013.01); *A61M 2230/42* (2013.01); *A61M 2230/50* (2013.01); *A61M 2230/60* (2013.01); *A61M 2230/65* (2013.01); *A63B 71/0622* (2013.01); *A63B 2024/0093* (2013.01); *A63B 2220/30* (2013.01); *A63B 2225/50* (2013.01); *A63B 2230/062* (2013.01); *A63B 2230/10* (2013.01); *A63B 2230/30* (2013.01); *A63B 2230/40* (2013.01); *A63B 2230/50* (2013.01); *A63B 2230/60* (2013.01); *A63B 2230/65* (2013.01); *G16H 20/70* (2018.01); *G16H 50/20* (2018.01)

METHODS AND SYSTEMS OF CONTROLLING A SUBJECT'S BODY FEATURE HAVING A PERIODIC WAVE FUNCTION

TECHNOLOGICAL FIELD

The invention relates to methods and systems for controlling and adjusting a body feature using computerized systems, thereby being capable of treating or inhibiting at least the symptoms of a disease or disorder.

BACKGROUND AND GENERAL DESCRIPTION

Health costs are soaring word wide and high personal and economical costs result in General Motors spending more in recent years on their worker's health than in metal. Adopting healthy behaviors can greatly contribute to general health and reduce the extensive financial and mental costs to the person, the employer and the state. The primary motivation underlying the proposed system is to increase adherence to health behavior among users who suffer from a variety of symptoms and health conditions requiring improvement (e.g., diabetes, hypertension, asthma, chronic pain, stress, etc.) through the digital devices the user use around the day (computers, tablets, mobiles, etc.)

Monitoring user's physiological indicators can reflect quantitatively the mental and emotional state accurately and in real time allow adaption and use of correcting health behaviors. The current technology is not being mass used because the main arena for those treatments (e.g. treatment of anxiety, depression, chronic pain, lung disease, etc.) is a dedicated clinic (e.g. psychologic clinic, pain clinic, etc.). This arena contributes to the creation of many obstacles ranging from financial barriers to space and time barriers. Moreover, from adoption of many health behaviors (such as: smoking cessation, healthy eating, exercise, breathing physiotherapy) till the result is achieved requires weeks, months or even years of practice. It is not enough to devote a concerted effort once a week for a few minutes; rather these techniques have to be implemented in daily life, and practiced every day (like brushing your teeth twice a day).

Adherence to medical care (e.g., drugs, physiotherapy) is estimated to only happen in about 30% of cases. This adherence level is very disturbing especially in the context of preventive health behavior adoption that has the capability to save substantial time and resources. Research has proven the huge health importance of physiological monitoring of various metrics (such as HRV) because they can give an indication of various health problems (e.g. HRV is a good indicator of lung function).

Currently, most software developed to encourage the adoption of health behavior requires dedicated and separate software (e.g. biofeedback games). This situation necessitated the increased development of new content (screens, games, sound clips, logs etc.) in order to maintain the high level of interest among users and motivate them time and again to adopt this behavior by using the software.

The separate treatment environment (e.g. clinic) creates a sterile environment which is disconnected from the user's daily life (this is the difference between brushing your teeth in your private bathroom compared with a dental appointment). Such an environment will not only put more obstacles for the user but impedes the ability to implement the desired behavior anytime and anywhere (e.g. there is a real difficulty applying tools successfully used to control anxiety in the clinic when taken into real life, such as during an actual test with test anxiety). Even in recent years as the technology has progressed and health programs have reached both PC and smartphone, these programs remain separate from the regular programs used throughout the day (e.g. a biofeedback relaxation application compared to the very frequent use of e-mail, web browser, or a video player). Not only does the user need to remember and choose to launch a separate application, but the user is asked to put aside all current tasks and open a separate dedicated application that requires his entire focus. This situation brings back the question of adherence to treatment which is in the heart of this discussion and highlights the acute need to find smart solutions to this complex problem.

The present invention provides a system and a method that can become an integral part of the usage of any IT device (e.g. computer, tablet, mobile . . . ), eliminating the need for a separate "sterile" treatment (for example in a clinic) and the "real world" where the human subject is working and functioning (and also suffering from a condition to be treated). In addition, the solution presented in the present application allows follow-up on the adherence to desired health behaviors. This innovative development gives a good answer to the challenges mentioned above—overcoming barriers of time, geography and economic resources along with a dramatic increase in the adoption of healthy behaviors in daily life of users, who are already interacting with technology which can now be programmed to help increase health.

DETAILED DESCRIPTION OF EMBODIMENTS

The human heart rate is constantly changing due to a variety of biological, physiological and physical variables, including time of day, amount of exercise, stress level, mood, health, breathing and more. Each time we exhale our heart rate decreases, and it raises when we inhale. Stress increases the heart rate, and relaxation decreases it. Further natural body rhythms also have a major impact on heart rate. These changes in heart rate, known as heart rate variability, can be used to measure health, stress, and to some extent emotional state.

Traditional forms of heart rate variability analyze a large amount of data, and since the heart beats only approximately once per second, having a large quantity of data often means analyzing 30 minutes or more of heart rate data to determine something about the heart rate variability. Sometimes data is taken for many hours. Heart rate variability biofeedback, often used to help people relax or shift emotional state, often uses approximately 30 seconds of heart rate data, allowing for quicker shifts in heart rate that can be shown on the screen to help people understand, and learn to control, their stress, breathing, or other physiological changes.

These forms of biofeedback generally use frequency analysis and require a large enough sample of data to accurately analyze heart rate frequency. Because of this it still often takes 10 seconds or more in order from when you relax or change breathing patterns before a change in heart rate variability can be measured.

The present invention provides systems and methods that enable a subject to learn and adopt healthy life behavior based on the physiological measurement of at least one body feature and the ability to control said at least one body feature with methods and systems of the invention.

Figure 1:
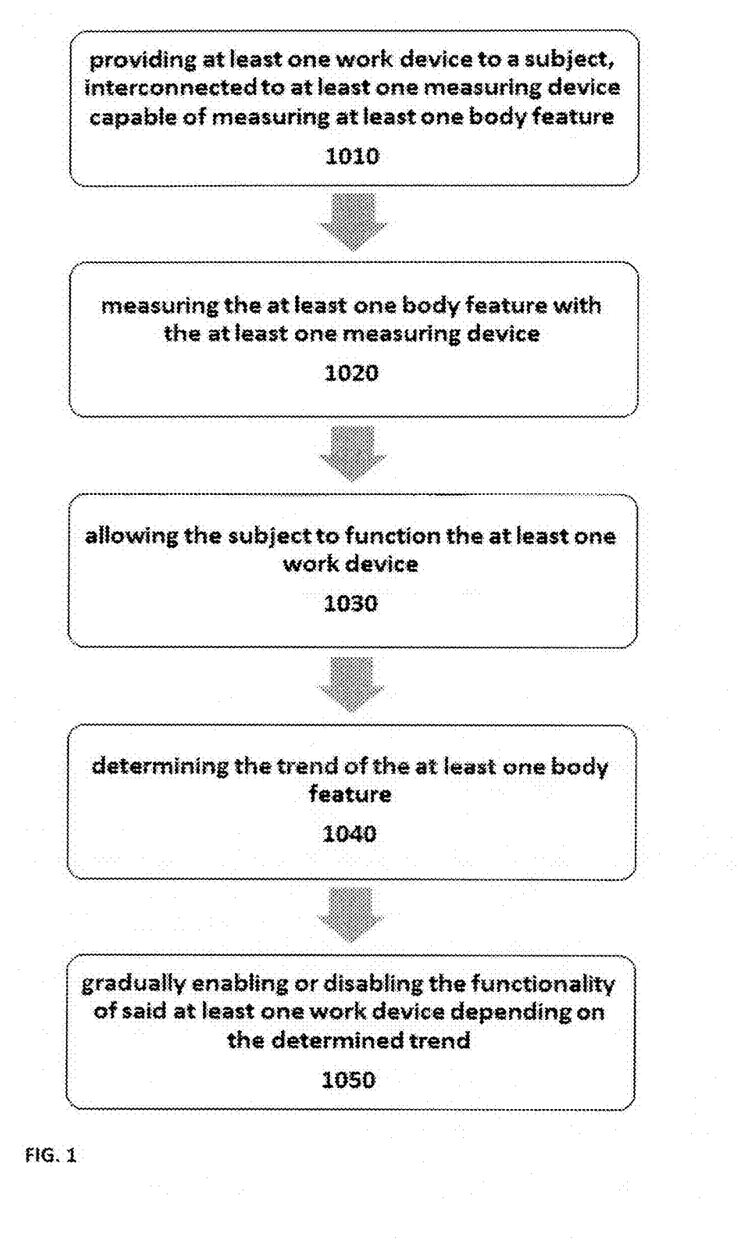
FIG. 1 illustrates method of controlling and/or adjusting at least one body feature of a subject according to some embodiments of the invention.

In FIG. 1, the present invention provides a method of controlling and/or adjusting at least one body feature of a subject comprising the steps of: (i) providing at least one work device to said subject interconnected to at least one measuring device capable of measuring said at least one body feature; (ii) measuring said at least one body feature with said at least one measuring device (iii) allowing said subject to function said at least one work device; (iv) determining the trend of said at least one body feature; (v) gradually enabling or disabling the functionality of said at least one work device depending on the trend of said measured at least one body feature; thereby controlling and/or adjusting the at least one body feature of said subject.

Figure 2:
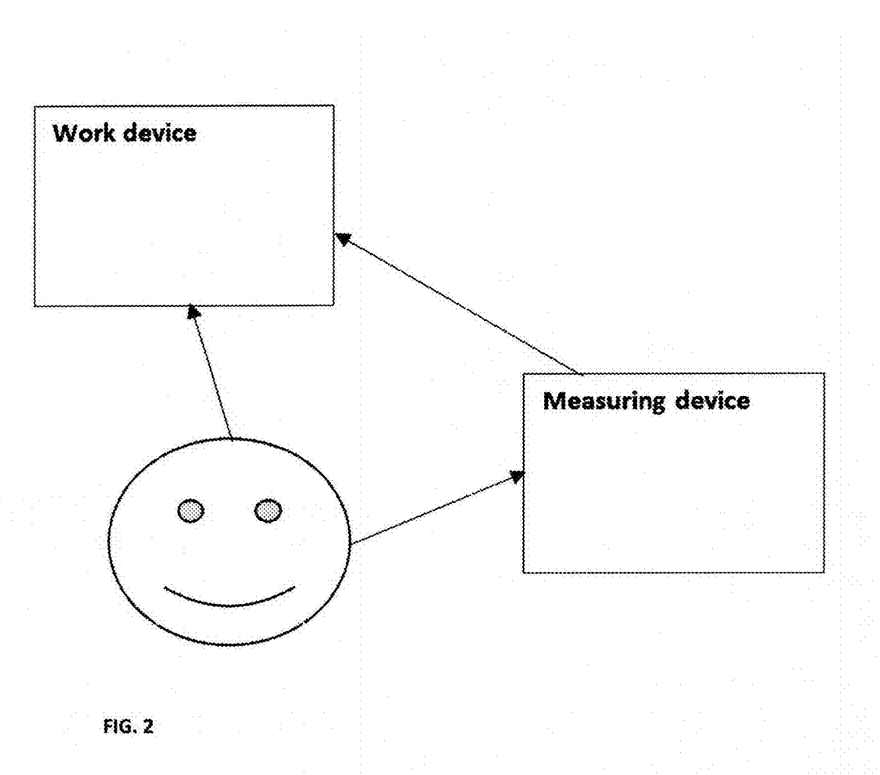
FIG. 2 exemplifies a system according to some embodiments of the invention.

The term "work device" encompasses any tool that the subject can function in a normal working or living environment and includes any device that is workable by said subject. This tool is not a medical clinically designated tool. The functionality of said work device is not pre-designated for a method of the invention, however the work device is equipped with a program that allows the interconnectivity with the measuring device of a method of the invention, receiving input and/or sending output from and to said measuring device and functioning according to the input received from said measuring device (FIG. 2). A subject is allowed to use the work device in a normal and usual manner he or she is using the device on a daily basis.

In some embodiments said work device is an electronically functioning tool that can be used by said subject. In some embodiments, said work device is a computer (either hand held, stationary or laptop device), a phone, a gaming port, an exercise machine, a gardening tool, a vehicle, and so forth (or a combinations thereof).

The term "measuring device" refers to any device that is capable of measuring said body feature. In some embodiments said measuring device comprises a sensor for measuring a body feature. Examples of such sensor include but are not limited to light, radio frequency, electromagnetic, and so forth (or any combinations thereof) It is noted that the measuring device is capable of providing the measure of said body feature in any way known in the art (for example by placing said sensor on the body of said subject or remotely sensing said body feature of said subject by said sensor). Examples of such devices include but are not limited to ECG, PPG, DLS, NIBP, GSR, EEG, EMG, temperature, and so forth (or any combinations thereof). The measuring device is interconnected with said work device, capable of sending output and/or receiving input from said work device (FIG. 2). In some further embodiments said measuring device and working device are placed in a single tool.

In some embodiments, said measuring device is a wearable device. Said "wearable device" comprises at least one sensor for obtaining physiological measurements with a transmitter which reports to at least one work device which performs one or more of the following actions: shows the user the current trend of said at least one measured body feature (indicating subject's current health state), in some embodiments guiding the user to change his or hers behavior in a manner that allows for the trend of the measured at least one body feature to become normal or healthy. This will teach said subject to adopt health behavior based on his physiological measurements.

In some embodiments said "wearable device" can be a smart watch with a heart rate sensor with a Bluetooth transmitter. In other embodiments said "electronic work tool" can be a smart phone, which shows the user his lung function based on the live heart rate measurement, guides the user on how to breath using an adaptive pacer, alerts the user when lung function is low, uses a gray out locking mechanism as an adherence mechanism. In other embodiments said "wearable device" can be a sensor patch equipped with a transmitter (such as for example Wi-Fi or Bluetooth).

The term "interconnected" as used herein is meant to encompass any type of connection between said measuring device and work device so as to send and receive input and output between them. Such interconnections allows for the measurement of said body feature made by the measuring device be received by said working device (in some embodiments such data is being presented graphically on said working device). In some embodiments said interconnection is a wireless connection, a wired connection, a Bluetooth connection, a WIFI connection, an NFC connection or any type of connection and enables the measured feature to be received by said work device.

The term "body feature" should be understood to encompass any human subject's bodily feature representative of a functioning human body. Such bodily features, when measured using standard equipment for measuring said bodily feature, can provide in input to the health state of said subject either generally or with specific respect to said bodily feature being measured.

According to the present invention the method disclosed herein determines the trend of said at least one body feature being measured, i.e. determining whether said at least one body feature being measured is showing a healthy trend or unhealthy trend (i.e. the direction of change in said measured at least one body feature that indicates whether the feature is showing healthy or unhealthy condition of said subject). This determination is based on the trend of said at least one body feature, whether the trend is raising or falling. The health and unhealthy determination of the trend can be either predetermined using medical knowledge of average and normal healthy levels or can be personally adjusted to the features of the subject being treated with a method of the invention.

In case the trend that is measured and determined shows that the at least one body feature of said subject is at an unhealthy trend, the working device is being gradually disabled, the graduability is influenced by the trend of said body feature. It is important to understand that the disablement of the work tool can be represented by gradually not allowing the subject to fully or partially function the work tool. For example in case the work tool uses a screen, the gradual disablement can be manifested by graying out or dimming the screen.

In case the trend that is measured and determined shows that the body feature of said subject is at a healthy trend, the working device is being gradually enabled, the graduability is influenced by the trend of said body feature. It is important to understand that the enablement of the work tool can be represented by gradually allowing the subject to fully or partially function the work tool. For example in case the work tool uses a screen, the gradual disablement can be manifested by clearing or brightening the screen.

The method of the invention allows for the control or adjustment of said measured at least one body feature.

The present invention provides a method of treating a symptom or condition of at least one disease or disorder selected from: cardiac conditions, respiratory conditions, physiological conditions, neurological conditions, oncological conditions, dermatological conditions, orthopedics conditions, hormonal conditions, mental health condition, orthopedic condition, vascular conditions, arterial conditions, somnipathy conditions, immune conditions, geriatric condition, pediatric conditions, and any combinations thereof; comprising the steps of: (i) providing a at least one work device to said subject interconnected to at least one measuring device capable of measuring at least one body feature related to said symptom or condition; (ii) measuring said at least one body feature with said at least one measuring device (iii) allowing said subject to function said at least one work device; (iv) determining the trend of said at least one body feature; (v) gradually enabling or disabling the functionality of said at least one work device depending on the trend of said trend of measured at least one body feature; thereby treating said symptom or condition.

The present invention provides a method of diagnosing the condition of a subject comprising the steps of: (i) providing at least one work device to said subject interconnected to at least one measuring device capable of measuring at least one body feature associated with at least one health condition of said subject; (ii) measuring said at least one body feature with said at least one measuring device (iii) allowing said subject to function said at least one work device; (iv) determining the trend of said at least one body feature; thereby diagnosing the health condition of said subject. In some embodiments, said diagnosis is outputted to said subject and/or a health care provider.

In some embodiments a method of the invention for controlling at least one body feature of a subject having a periodic wave function comprises the steps of: (i) providing at least one work device to said subject interconnected to at least one measuring device capable of measuring said at least one body feature; (ii) placing (either directly or remotely) said at least one measuring device on said subject and allowing said subject to function said at least one work device; (iii) measuring the variability of the rate of said at least one body feature using at least three points in the function's rate; (iv) gradually enabling or disabling the functionality of said at least one work device depending on the variability measurement; thereby controlling said at least one body feature.

The term "body feature having a periodic wave function" should be understood to encompass a human subject's bodily feature representative of a functioning human body organ that has a periodic wave function i.e. that repeats its values in regular intervals or periods. Such bodily features, when measured using standard equipment for measuring said bodily feature, can provide in input to the health state of said subject either generally or with specific respect to the organ producing the bodily feature being measured.

When referring to "controlling of body feature" it should be understood to encompass the ability of the methods and systems of the invention to direct the degree (either quantitative or qualitative) of said body feature (elevate it, reduce it or maintain it). In some embodiments, the control of said feature using a method and a system of the invention causes said body feature to function in a predetermined way (elevate it, reduce it or maintain it).

In some embodiments, said body feature is selected from heart rate, blood pressure, breathing rate, subcutaneous pH, sweat/saliva pH, brain waves, fetus heart rate, body temperature, muscle vibration, glucose/ketone levels (either in blood or urine), galvanic skin response or any combinations thereof.

In some embodiments, the trend or variability of the rate of said at least one body feature (for example the HRV) is measured using at least three points in the function's rate. It is noted that periodical body feature typically has points that return in every sequence, measuring the time difference between these points can be used to calculate the rate of said body feature. For example in a sinusoidal pattern the time between two peaks or the time between two valleys. For example in the case of electrocardiography wave RR-intervals, QQ-intervals, SS-intervals, PP-intervals, TT-intervals.

Depending on the measured variability, which in turn indicated the health situation of said subject, the method of the invention allows the gradual enablement or disablement of the functionality of said work device. Since the subject will want to enable to work device while working and functioning it, said subject will make an effort to alter the measured at least one body feature to a level or trend that enables the work device. This allows for the control of said at least one body feature.

Figure 3:
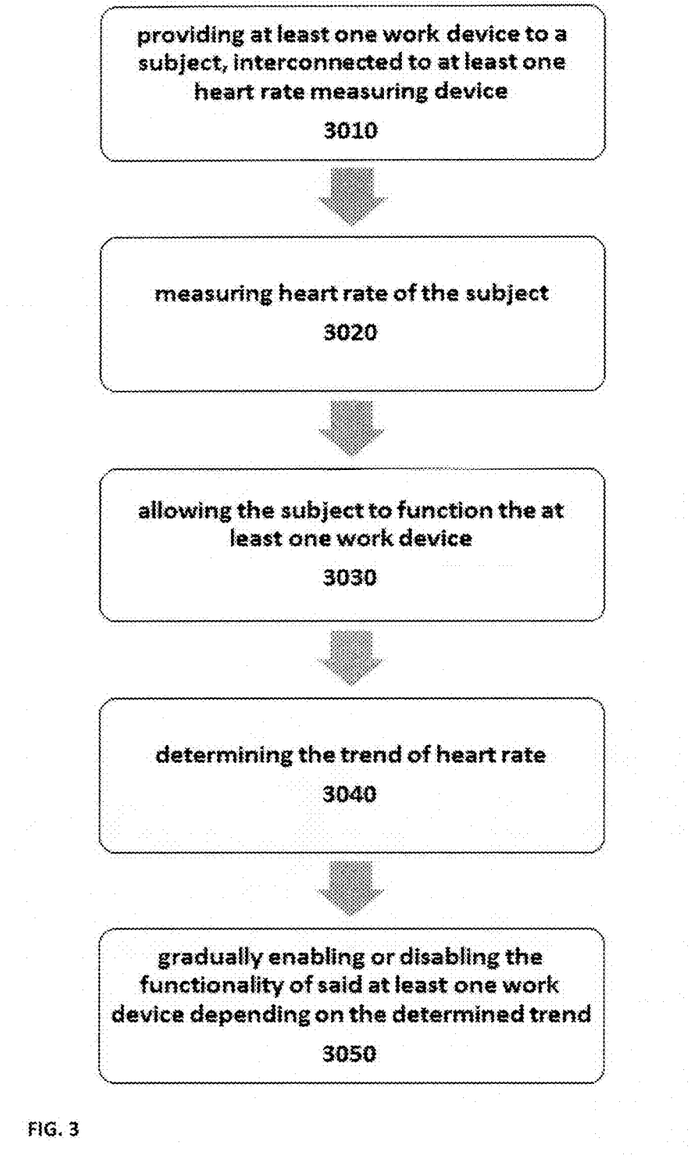
FIG. 3 illustrates method of controlling and/or adjusting at least one body feature of a subject according to some embodiments of the invention.

In a further embodiments, illustrated in FIG. 3, the method of the invention for controlling the heart rate of a subject comprising the steps of: (i) providing at least one work device to said subject interconnected to at least one measuring device capable of measuring said subject's heart rate; (ii) measuring said subject's heart rate with said at least one measuring device (iii) allowing said subject to function said at least one work device; (iv) determining the trend of said subject's heart rate; (v) gradually enabling or disabling the functionality of said at least one work device depending on the trend of said measured heart rate; thereby controlling and/or adjusting the heart rate of said subject.

Figure 4:
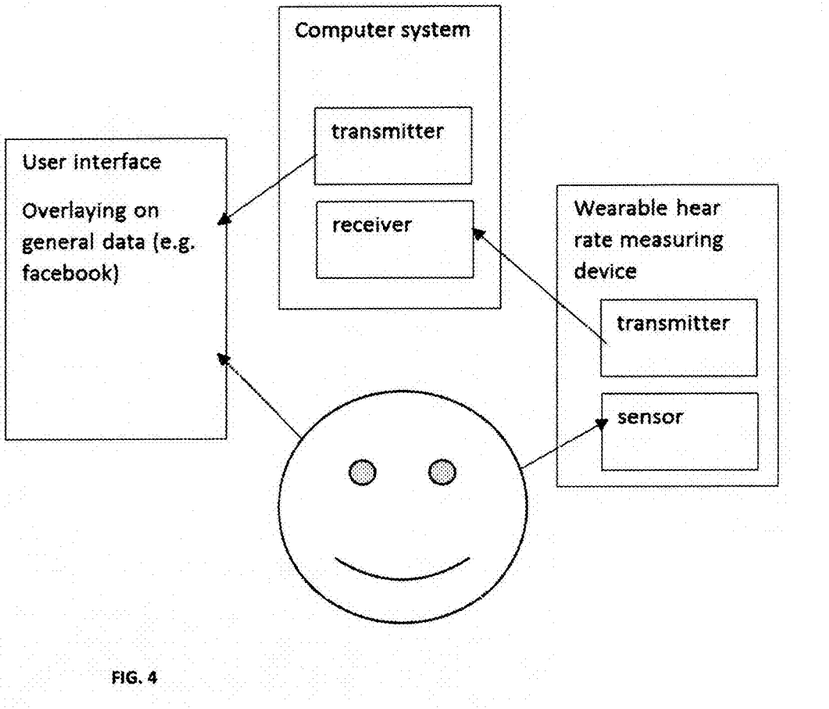
FIG. 4 illustrates a system according to some embodiments of the invention.

In some embodiments, shown in FIG. 4, a system operating the method of the invention comprises: at least one wearable device placed on the subject's body or located close to the subject's body including at least one dedicated physiological measurement sensor and at least one transmitter; a computer system including a transmitter and a receiver for receiving the physiological measurement from the wearable device and transmitting user guidelines; a local unit which includes a visual or audible user interface to present the user with the information or guidance received from the computer system.

The computer system operating the method of the invention performs one or more from the following actions according to predefined criteria: monitor and capture physiological data from the wearable device, analyzing the data to identify health issues, notifying the local unit of health status, send guidance to local unit for improvement of health status, monitor the compliance to the guidance, adherence mechanism which interfere with local unit regular work to prompt health behavior if compliance is low.

In some other embodiments a system operating the method of the invention comprises: at least one wearable device placed on a subject body or located close to the body including at least one dedicated physiological measurement sensors and at least one transmitter, a local computer system including at least one transmitter and at least one receiver for receiving the physiological measurement from the wearable device and transmitting user guidelines, as well as a visual or audible user interface to present the user with the information or guidance.

In some embodiments, the local computer system operating the method of the invention performs one or more from the following actions according to predefined criteria: monitor and capture physiological data from the wearable device, analyzing the data to identify health issues, notifying the user of health status, send guidance to the user for improvement of health status, monitor the compliance to the guidance, adherence mechanism which interfere with the local computer system's regular work to prompt health behavior if compliance is low.

In some further embodiments, a system operating a method of the invention comprises: at least one wearable device placed on the subject's body or located close to the body including at least one dedicated physiological measurement sensor and at least one visual or audible user interface.

Under these embodiments the wearable device performs one or more from the following actions according to pre-defined criteria: monitor and capture physiological data, analyzing the data to identify health issues, notifying the user of health status, send guidance to the user for improvement of health status, monitor the compliance to the guidance, adherence mechanism which interfere with the wearable devices visual or audio functionality work to prompt health behavior if compliance is low.

In some embodiments the computer system can be located in a remote cloud system. In other embodiments, the computer system can accept input from multiple wearable devices and send data to multiple local units. In further embodiments, the local computer system can accept input from multiple wearable devices. In further embodiments, the wearable device can be installed as a bracelet hand or foot. In other embodiments, the wearable device can be installed as a patch on the body. In other embodiments, the wearable device can be worn on the ear. In further embodiments, the wearable device can be a glove, a ring, a chest strap, a head strap or patch. In some embodiments, the wearable device measures PPG, DLS, BVP, EKG, Temperature, GSR, Glucose, SpO2, blood pressure or other physiological measurements. In some further embodiments, the local unit may be a mobile Smartphones, tablet, computer, watch, projected display, laptop, desktop, or other.

The method of the invention is designed to support, treat or control the health behavior of a subject suffering from at least one of the following indications: lung function (e.g. asthma, COPD) that can be based on heart rate sensor or other, stress or anxiety or depression or PTSD that can be based on heart rate sensor and/or galvanic skin response sensor or other, diabetics that can be based on glucose sensor or eating sensor or other, sleep disorder based on motion sensors or other, hypertension that can be based on heart rate sensors and blood pressure sensor or other, chronic pain that can based on heart rate sensor or other sensors.

Figure 5:
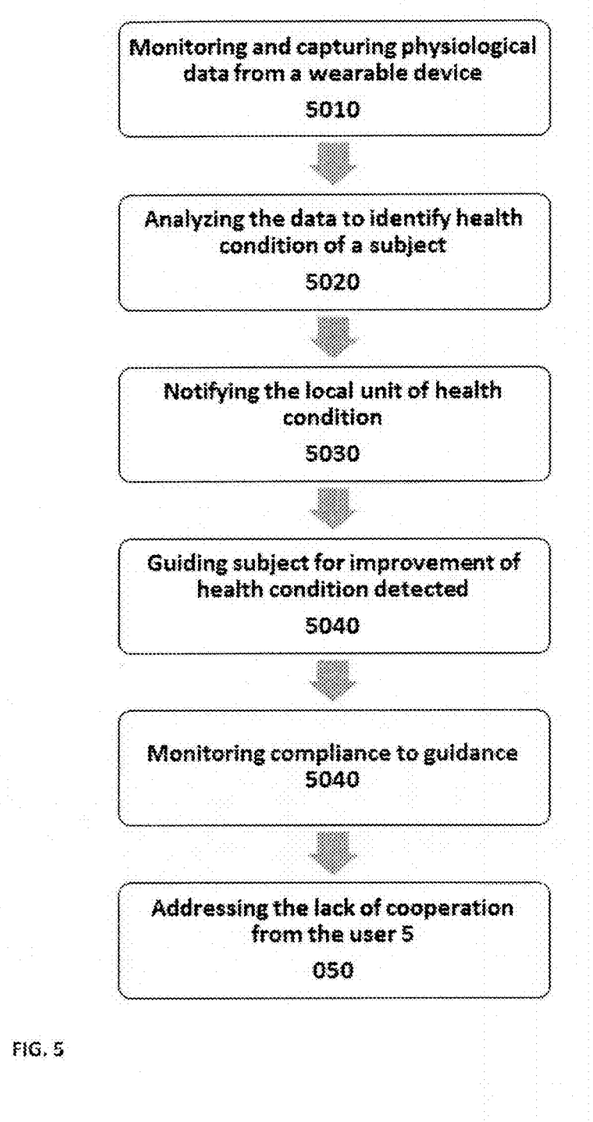
FIG. 5 illustrates a method according to some embodiments of the invention.

Thus, a method of the invention is designated to treat, inhibit, control or eliminate symptoms and conditions associated with at least one of the following diseases asthma, COPD, stress, anxiety, depression, PTSD, diabetes, sleep disorders, hypertension, cardiovascular conditions, pain and so forth. The method of the invention controls and regulates at least one body feature associated with at least one of the above mentioned diseases thereby controlling, treating or inhibiting or eliminating a symptom or condition associated therewith. FIG. 5 illustrates:

Monitoring and Capturing Physiological Data from a Wearable Device:

the computer system monitors and captures physiological measurements (e.g. live heart rate, galvanic skin conduction, etc.) from different wearable device/s sensor/s. Physiological indicators can reflect a wide range of health conditions (such as asthma severity, diabetes severity, chronic pain, fatigue etc.) along with complex mental states (such as depression, anxiety, post-traumatic stress disorder, etc.). For example, in the case of lung disease we know that the relation between asthma severity and HRV score, making this measure a good indicator of asthma condition in general and in real time.

Analyzing the Data to Identify Health Condition of a Subject:

the system identifies the health condition of a subject by analyzing the captured physiological measurement data, transforming it into physiological indicators (e.g. lung function, stress, diabetic and so forth). Analysis focuses on certain patterns or a certain limits referenced and related to known standards or user-specific patterns. For example: from heart rate data the computer system calculate the heart rate variability (HRV) score, which is used as an indicator for lung function, this indicator is compared to know norms and user norms and patterns so the system can know that in a certain time a lung function issue is evolving for a lung patient which has a low norm of HRV in any case.

Notifying the Local Unit of Health Condition:

when the system identifies a problematic situation it sends an alert to the user or a care provider about the current situation. For example by popping open an information bubble on the screen—without changing the current used application. For example, a patient with a lung disease that travels in an area with severe air pollution (at a busy intersection, smoke-filled room) will be notified in real time on a decline in physical resilience and a weakening of his respiratory system. See FIG. 4 where the patient is using Facebook and receives a notification and information overplayed on his current application.

Guiding Subject for Improvement of Health Condition Detected:

the system offers guidance to adopt a health behavior that can improve the user's current state, such as coherent breathing where respiratory rate is synchronized with heart rate. This solution also displays as a pop over the user's current working application. For example a patient with lung disease receives instructions to help him carry out immediate breathing physiotherapy—exactly when to breathe in and exhale in relation to the heart live rhythm.

Monitoring Compliance to Guidance:

if the user decides not to comply with the suggested guidance, the user can choose to postpone the notification to a later time, while the system continue to monitor the user and send notification to comply with the guidance as appropriate. The user can elect when he wants to comply with the guidance within a predefined time frame (e.g. until midnight) or decide when the system will reminder him again. The system can also detect the actual implementation of the guidance. For example, the system not only "remembers" a lung patient has selected to postpone the implementation of guidance until a later time, but if the patient is in the middle of a busy intersection it can decide to remind the user to practice breathing in about 15 minutes based on his current place and activity, and notify him upon arrival to the office.

Addressing the Lack of Cooperation from the User:

after a period defined in advance and/or a significant deterioration in physiological indictors, if the user chooses not to implement the solution offered to him, the system can gray or lock certain applications and/or certain pre-defined devices and operation can then be resumed only after compliance with guidance and the improvement of physiological indicators. For example, for a lung disease patient that until the end of his work day does not practiced the coherence breathing guidance, the system will then lock a commonly used social application like Facebook and it will be inaccessible until after he complies with the breathing exercises. This step is intended to ensure that the response to the challenges mentioned above, first and foremost it is vital to ensure persistence in adopting the desired health behaviors. Many people say they need external factors to help them live a healthy lifestyle, and would like a framework to guide and force them firmly to change habits, and if necessary even reprimand them for wrong behavior.

In some embodiments, a system operating a method of the invention comprises: at least one wearable device placed on the subject's body or located close to the body that measure heart rate changes (heart rate variability), a computer system to process the data from the wearable device. The computer system can be separate from or part of the wearable device. Under these embodiments a computer system performs one or more of the following actions according to predefined criteria: analyzes the heart rate variability to extract one or more components that can be used to show momentary stress level changes, breathing or any short term changes that occur in 1 minute or less, analyzes the heart rate variability to extract one or more components that are due to longer term changes, health, circadian rhythms or any longer term changes that occur in 1 minute or more; calibrates the momentary changes using the long term changes.

In some embodiments, a system for operating a method of the invention accurately calibrates combination of a heart rate variability (HRV) algorithm that rapidly detects and optionally displays changes in stress, relaxation, and other physiological, emotional or any changes of a user, where the calibration of that algorithm is based on longer term measurements of heart rate variability of that user, to eliminate, utilize, display separately or utilize separately or in combination with heart rate variations detected based on time of day, health, exercise, emotional state or any other factor that contributes to influences heart rate changes. The algorithm calibrates constantly, occasionally, or has an initial calibration time, so as to display ideal information to a user, and give them useful absolute feedback (such as amount of stress) or relative feedback (such as when their stress levels are increasing).

In some embodiments, the algorithm is used in conjunction with an electronic game, where a subject needs to relax or adjust the breathing, psychological or physiological state in order to play or win. Using the combination of short term and long term data, the system of the invention accurately calibrates the feedback to make training enjoyable. Without this calibration users would sometimes have a harder time playing the game, or controlling their heart rate variability, due to factors that are not taken into account in heart rate variability biofeedback, such as time of day, health or other factors. Therefore users will have a more enjoyable time training, use the software more, and have more benefits of being able to accurately understand and train to control their stress level, emotional state, or any other possible training use of heart rate variability.

Another example use of this algorithm is for long term tracking of a user's state, where we track not only major shifts in HRV, but also track the short term changes in HRV which indicate momentary changes in emotional state and stress level. For example these could be correlated with other inputs from other sensors, or data on a smartphone, so heart rate variability can be correlated with movement, activity, time of day, phone calls, scheduled events such as meetings, or any other data available. This information could then be analyzed, aggregated amongst many users, and/or displayed to the user, their employer, or any third party. The combination of a calibrated HRV measurement that can display momentary stress changes, calibrated using a longer term measurement of HRV, allows for an increased amount of data and increased usefulness of that data, both for display to the user or use in any other ways, including those described above.

Another example use of this algorithm can be to improve breathing or lung function. Heart rate variability can be used to measure the speed, quality or other attributes of breathing, and HRV feedback can be used as a way to give users feedback about the speed and quality of their breathing. By using our calibrated HRV algorithm we can accurately inform users as to the quality of their breathing, help them improve breathing, and/or help them improve lung function. Without a calibrated algorithm if a user is having a day where the lung function is poor, health is poor, or for any reason their HRV is different, they may be doing useful breathing exercises but the resulting HRV would show that they are not breathing correctly. A calibrated algorithm can focus specifically on HRV changes related to their momentary changes in breathing, separating out the data that their lung function is not as well for that specific day, but still giving them useful feedback as they improve their breathing in that moment. Without that useful feedback users may simply not train when their lung function is poor, as no matter what they do they would be unable to sufficiently alter their HRV. This would prevent them from training specifically during the time periods that are most important, so an algorithm that adapts to the user's changes in a way that allows the user to see their improvements separately from their overall state, or any other factor that influences HRV, is a very important improvement in HRV training for breathing, lung function, or to give any user useful feedback without confusion.

Another example of this algorithm is to take the HRV and separate out various components, showing the HRV changes due any one or more of the following separately, or at least partially separating the influences of any one or more of the following: breathing, stress levels, relaxation levels, emotional state, mental state, physical activity, time of day, circadian rhythm, specific events such as phone calls, meetings, etc., and/or other physiological rhythms.

In some embodiments, a system and a method of the invention is capable of analyzing and adjusting a breath pacer using heart rate data.

Under these embodiments a system for operating a method of the invention comprises: at least one wearable device placed on the subject's body or located close to the body that measure heart rate changes (heart rate variability), a computer system to process the data from the wearable device. The computer system can be separate from or part of the wearable device.

Under these embodiments, the computer system performs one or more of the following actions according to predefined criteria: displays a visual or auditory pacer that indicates how quickly to breathe or when to breathe in, out, or optionally hold the breath, analyzes the heart rate and adjusts the pacer based on heart rate changes, a visual, auditory or kinesthetic cue given to guide a user when to breathe in and out. This could be a line moving up and down (where when the line moves up you breathe in and when the line moves down you breathe out) a 3D object expanding and contracting in a game, a series of tones, or any other cue to guide a user when to breathe.

Breath pacers are commonly displayed as a line moving up and down at a fixed rate. Our unique breath pacer uses the heart rate changes to update the cues given to the user as to when to breathe. When a user is breathing in, their heart rate naturally rises, and when a user is breathing out, their heart rate naturally falls. Using this information if, during an in breath, the heart rate falls, or during an out breath, the heart rate rises, we can use this information to fine tune the pacer speed, or make an immediate change in the pacer to reflect the user's heart rate changes. If during an out breath the user's heart rate rises, this indicates that the breath may be too long, as the increased heart rate can be due to the strain of breathing out for too long, or the increase can simply indicate the user is ready to inhale again. Therefore using the heart rate data to modify the breath pacer helps the breath pacer be more accurate. In addition, a standard breath pacer must be set for a specific time interval, such as 10 seconds per breath. Users don't know what speed to set the pacer to (there is no easy way for beginners to choose a speed), and the ideal pacer speed changes over time in ways that users are not aware of. Therefore standard pacers have the issue of what speed to use, and don't have a good solution for either user's choosing their own speed, or the software choosing a speed for the user. Our adaptive pacer that adapts to the users heart rate changes allows users to not think about setting a particular speed, and to simply start training. This is especially important for mobile where users expect apps to be simple, work immediately and where they may not have extra time to attempt to manually adjust a pacer. Furthermore over time as the body relaxes into breathing more slowly, the pacer should help the user breathe at slower speeds. Most users forget to lower the pacer, so having the pacer automatically lower itself is vital for many users who need to be guided into slower breathing over time. The pacer must start relatively fast, and slow down when the user is ready for a slower pace, as shown by the heart rate changes during the in and out breaths.

The invention claimed is:

1. A method for use in assisting a user to control at least one body feature of a subject, said at least one body feature comprises heart rate variability, the method comprising:
   providing a user with at least one work device comprising a computer system providing at least one of audio and visual functionality, and at least one heart measuring device, said at least one work device being connected to said at least on heart measuring device to receive data indicative of measured heart rate of the user from said at least one heart rate measuring device;
   continuously measuring user's heart rate using said at least one heart rate measuring device;
   transmitting data indicative of measured heart rate to said at least one work device, and using said computer system for determining trend comprising heart rate variability based on said data indicative of heart rate;
   gradually enabling or disabling the at least one of audio and visual functionality of said at least one work device depending on the trend of said heart rate, thereby encouraging the user to control heart rate variability thereof.

2. The method of claim 1, wherein gradually enabling or disabling the at least one of audio and visual functionality of said at least one work device comprises clearing or brightening screen of said at least one work device.

3. The method of claim 1, wherein gradually enabling or disabling the at least one of audio and visual functionality of said at least one work device comprises varying brightness of screen of said at least one work device.

* * * * *